US009527081B2

(12) United States Patent
Gibson et al.

(10) Patent No.: US 9,527,081 B2
(45) Date of Patent: Dec. 27, 2016

(54) CHIMERIC DNA IDENTIFIER

(71) Applicant: Advanced Tactical Ordnance LLC, Abbeville, MS (US)

(72) Inventors: Gary E. Gibson, Riverswood, IL (US); Benjamin Tyler Tiberius, Fort Wayne, IN (US)

(73) Assignee: UNITED TACTICAL SYSTEMS, LLC, Lake Forest, IL (US)

( * ) Notice: Subject to any disclaimer, the term of this patent is extended or adjusted under 35 U.S.C. 154(b) by 0 days.

(21) Appl. No.: 13/771,700

(22) Filed: Feb. 20, 2013

(65) Prior Publication Data
US 2013/0217025 A1 Aug. 22, 2013

Related U.S. Application Data

(60) Provisional application No. 61/600,710, filed on Feb. 20, 2012.

(51) Int. Cl.
*C12M 1/00* (2006.01)
*B01L 3/00* (2006.01)
*G01N 33/53* (2006.01)
*C12Q 1/68* (2006.01)
*B01J 19/00* (2006.01)
*F42B 12/40* (2006.01)
*F42B 10/06* (2006.01)

(52) U.S. Cl.
CPC ............ *B01L 3/52* (2013.01); *B01J 19/0046* (2013.01); *C12Q 1/686* (2013.01); *C12Q 1/6813* (2013.01); *F42B 10/06* (2013.01); *F42B 12/40* (2013.01); *G01N 33/5308* (2013.01)

(58) Field of Classification Search
CPC ............ C12Q 1/6813; C12Q 2547/101; C12Q 2563/185; C12Q 1/686; B01J 19/0046; B01L 3/52; F42B 10/06; F42B 12/40; G01N 33/5308
USPC ..................................... 435/283.1
See application file for complete search history.

(56) References Cited

U.S. PATENT DOCUMENTS

| 5,036,006 A * | 7/1991 | Sanford ............... C12M 35/04 |
| | | 435/235.1 |
| 5,906,686 A * | 5/1999 | McNeil .......................... 134/1 |
| 7,098,031 B2 * | 8/2006 | Choulika et al. ............ 435/455 |
| 7,815,868 B1 * | 10/2010 | Jones et al. .................. 422/129 |
| 2005/0177098 A1 * | 8/2005 | Lin et al. ........................ 604/68 |
| 2006/0110756 A1 * | 5/2006 | Tang et al. ...................... 435/6 |
| 2010/0218695 A1 | 9/2010 | Kirkpatrick et al. |
| 2012/0199034 A1 * | 8/2012 | Gibson ................. F42B 12/40 |
| | | 102/502 |

FOREIGN PATENT DOCUMENTS

| EP | 2135674 | 12/2009 |
| WO | PCT/US1999/026211 | 8/2000 |
| WO | WO03/080931 | 10/2003 |
| WO | PCT/EP2010/055473 | 10/2010 |
| WO | WO2012/003348 | 1/2012 |

OTHER PUBLICATIONS

International Search Report dated Jun. 14, 2013 for related International Patent Application No. PCT/US2013/026870.
Cox, Jonathan P. L., "Bar Coding Objects With DNA", The Analyst, vol. 126, No. 5, Jan. 1, 2001, pp. 545-547.
Supplemental European Search Report for related European Patent Application No. 13751698.5, mailed Sep. 28, 2015.

* cited by examiner

*Primary Examiner* — Cynthia B Wilder
(74) *Attorney, Agent, or Firm* — McDermott Will & Emery LLP

(57) ABSTRACT

Devices and methods for delivering a chimeric deoxyribonucleic acid (DNA) marking agent to a target and identifying the target from the chimeric DNA marking agent are provided. A delivery device may be a projectile, a spray canister or a wet/dry article. The chimeric DNA marking agent includes unique DNA fragments and may also include a fill material such as a liquid, a gas or a powder. The chimeric DNA marking agent may be combined with any combination of general marking agent, an inhibiting agent, an immobilizing agent, a weighting agent and a protective agent. The DNA marking agent may be analyzed using any of a hybridization method utilizing a labeled probe, a gel electrophoresis method, determining the base sequence to confirm a predefined DNA sequence, amplifying at least one of the unique DNA fragments and using a polymerase chain reaction (PCR) method.

15 Claims, 3 Drawing Sheets

CHIMERIC DNA IDENTIFIER

CROSS-REFERENCE TO RELATED APPLICATIONS

This application claims priority to U.S. Provisional Patent Application No. 61/600,710, entitled "CHIMERIC DNA IDENTIFIER," filed Feb. 20, 2012, the disclosure of which is incorporated herein in its entirety by reference.

TECHNICAL FIELD

The present invention relates generally to marking projectiles, inhibiting sprays, and wipes, and more particularly to marking projectiles, inhibiting sprays, and wipes having a chimeric DNA identifying agent.

BACKGROUND OF THE INVENTION

Marking projectiles, inhibiting sprays and wipes are well known in the art. While traditional marking projectiles, inhibiting agents and wipes according to the prior art provide a number of advantages, they nevertheless have certain limitations. For example, it is generally not known who or when the marking projectiles, inhibiting sprays and wipes were used. The present invention seeks to overcome certain of these limitations and other drawbacks of the prior art, and to provide new features not heretofore available.

SUMMARY OF THE INVENTION

The present invention seeks to utilize a new method of identifying the product used to mark a target, such method being a chimeric DNA marking or identifying agent. This chimeric DNA marking/identifying system can be used in place of the general marking agents described above or in combination with the general marking agents. If the chimeric DNA marking/identifying agent is used in combination with the general marker, it can be either combined in the same solution as the marker or in a separate solution located in a separate chamber of the projectile. Additionally, the chimeric DNA marker/identifier can be used in combination with an immobilizing agent. The immobilization agent may be in the same solution with the markers or in a separate solution. Examples of immobilizing components include liquid irritants, powder irritants, gaseous irritants, pepper powders, tear gas, malodorants, and other noxious chemicals These chimeric DNA marking/identifying agents can also be utilized in other devices that can transfer the chimeric DNA marking/identifying agent onto the target. Such devices could be a spray canister. The spray canister can contain just the chimeric DNA marking/identifying agent alone or in combination with an additional agent such as a general marking agent, an inhibiting agent, and/or an immobilizing agent. Examples of inhibiting agents include pepper powder or liquid, tear gas, malodorants, or anything that is used in an attempt to modify the behavior of animals, including humans. Examples of immobilizing components include liquid irritants, powder irritants, gaseous irritants, pepper powders, tear gas, malodorants, and other noxious chemicals.

Another device that can utilize the chimeric DNA marking/identifying agent includes wipes, cloths, swabs, or gloves, or other objects that contain a liquid or dry delivery agent containing the chimeric DNA marking agent. These devices can mark the target by coming in physical contact with the target.

The marked target can then be identified by detection of the particular chimeric DNA samples found on the target. Detection can occur by, e.g., collection, amplification, and analysis of the samples. One method of amplification of the DNA sample comprises a PCR method. One method of analysis comprise detecting the size of the DNA fragment using techniques such as gel electrophoresis or determining the base sequence to confirm a predefined DNA sequence. Alternatively, the DNA fragments may be detected by e.g., a hybridization method using a labeled probe. Additional known methods of collecting and analyzing samples are well known in the art.

According to one embodiment of the invention, a delivery device for delivering a chimeric deoxyribonucleic acid (DNA) marking agent to a target is provided. The delivery device includes a housing and a chimeric DNA marking agent, wherein the chimeric DNA marking agent comprises two or more unique DNA fragments.

According to an aspect of the invention, the chimeric DNA marking agent includes a fill material including one or more of a liquid, a gas and a powder. According to another aspect of the invention, the delivery device also includes a general marking agent. According to yet another aspect of the invention, the delivery device also includes an inhibiting agent. According to still another aspect of the invention, the delivery device also includes an immobilizing agent. According to another aspect of the invention, the delivery device also includes a weighting agent. According to yet another aspect of the invention, the delivery device also includes a protective agent.

According to another aspect of the invention, the housing is a projectile. According to yet another aspect of the invention, the projectile includes a spherical body and a single cavity configured to be at least partially filled with the chimeric DNA marking agent. According to still another aspect of the invention, the projectile includes a hemispherical body portion, a cylindrical body portion and a single cavity configured to be at least partially filled with the chimeric DNA marking agent. According to another aspect of the invention, the projectile includes a hemispherical body portion having a first cavity, a cylindrical body portion having a second cavity and a divider separating the first cavity from the second cavity, wherein at least one of the first cavity and the second cavity is configured to be at least partially filled with the chimeric DNA marking agent, and wherein at least one of the first cavity and the second cavity is configured to be at least partially filled with one of the general marking agent, the inhibiting agent, immobilizing agent, the weighting agent and the protective agent. According to another aspect of the invention, the housing is a spray canister. According to yet another aspect of the invention, the housing is a moist article comprising one of a wipe, a cloth, a swab, a duster and a glove. According to still another aspect of the invention, the housing is a dry article comprising one of a wipe, a cloth, a swab, a duster and a glove.

According to another embodiment of the invention, a method of identifying a target using a chimeric deoxyribonucleic acid (DNA) marking agent is provided. The method includes using a delivery device to mark a target with a chimeric DNA marking agent. The method also includes collecting two or more unique DNA fragments from the chimeric DNA marking agent on the target. The method further includes analyzing the two or more unique DNA fragments to identify each unique DNA fragment. The method also includes determining the identity of the chimeric DNA marker based on the analysis.

According to an aspect of the invention, the using the delivery device includes one of shooting a projectile at the target, spraying the target with a spray canister and wiping the target with one of a wet article and a dry article. According to another aspect of the invention, the method further includes identifying the delivery device that marked the target based on the determined identity of the chimeric DNA marker. According to yet another aspect of the invention, the analyzing the two or more unique DNA fragments includes one of a hybridization method utilizing a labeled probe, a gel electrophoresis method and determining the base sequence to confirm a predefined DNA sequence. According to still another aspect of the invention, the analyzing the two or more unique DNA fragments includes amplifying at least one of the unique DNA fragments and using a polymerase chain reaction (PCR) method.

According to yet another embodiment of the invention, a delivery device for delivering a chimeric deoxyribonucleic acid (DNA) marking agent to a target is provided. The delivery device includes a housing including a body defining at least one cavity and at least one fill hole, wherein at least a portion of the body is spherical. The delivery device also includes a fill material including one of a liquid, a gas and a powder. The delivery device further includes a DNA marking agent, wherein the DNA marking agent includes one or more unique DNA fragments. The delivery device also includes at least one of a general marking agent, an inhibiting agent, an immobilizing agent, a weighting agent and a protective agent.

A full discussion of the features and advantages of the present invention is deferred to the following detailed description, which proceeds with reference to the accompanying drawings.

BRIEF DESCRIPTION OF THE DRAWINGS

To understand the present invention, it will now be described by way of example only, not by way of limitation, with reference to the accompanying drawings in which:

FIG. 1b is a cross-sectional view along the line 1b of the projectile of FIG. 1a;

FIG. 2b is a bottom perspective view of the aerodynamic projectile of FIG. 2a; and, FIG. 2c is a cross-sectional view along line 2c of the projectile of FIG. 2a.

DETAILED DESCRIPTION

Figure 1A:
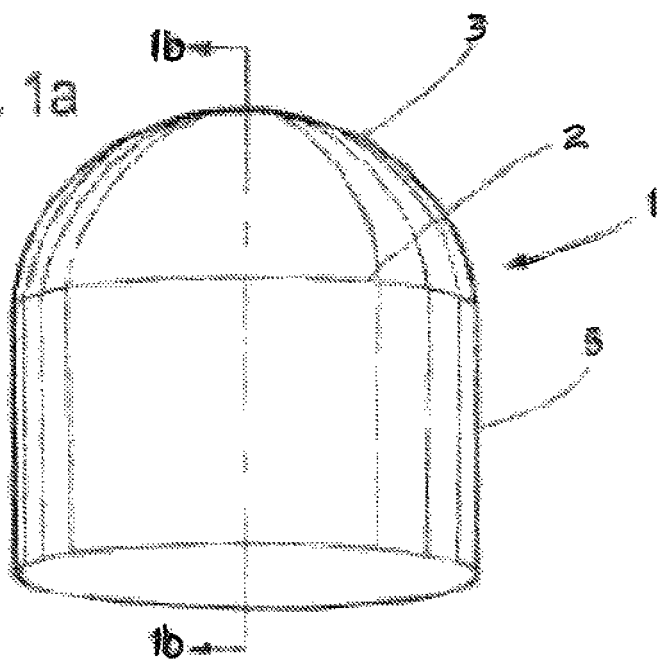
FIG. 1a is a perspective view of one embodiment of an aerodynamic projectile having a chimeric DNA marking agent.

While this invention is susceptible of embodiments in many different forms, there is shown in the drawings and will herein be described in detail embodiments of the invention with the understanding that the present disclosure is to be considered as an exemplification of the principles of the invention and is not intended to limit the broad aspect of the invention to the embodiments illustrated.

Several alternative embodiments and examples have been described and illustrated herein. A person of ordinary skill in the art would appreciate the features of the individual embodiments, and the possible combinations and variations of the components. A person of ordinary skill in the art would further appreciate that any of the embodiments could be provided in any combination with the other embodiments disclosed herein. Further, the term "plurality" as used herein indicates any number greater than one, either disjunctively or conjunctively, as necessary, up to an infinite number. Additionally, the term "having" as used herein in both the disclosure and claims, is utilized in an open-ended manner.

Referring now to the different embodiments of the invention, various embodiments of projectiles, sprays, wipes, and other marking media are provided having a chimeric DNA identifying or marking agent. As describe herein, the term chimeric DNA identifying or marking agent refers to a combination of two or more unique DNA (deoxyribonucleic acid) fragments or samples. The DNA fragments of the chimeric DNA marking agent may be found in a medium or fill material, such as a liquid solution, a gas or a powder, for example. These DNA fragments can be from any species or synthesized to form a DNA fragment with a sequence not found in a particular species. These DNA fragments may be single stranded or double stranded. The DNA fragments are preferably produced using recombinant DNA technology (e.g., polymerase chain reaction (PCR) amplification, cloning, etc.) or chemical synthesis.

Preferably, the DNA fragments differ from each other in some detectable way. For example, the DNA fragments can differ in the sequence of nucleotides and/or in the number of nucleotides which make up the DNA fragment (i.e, the length/size of the DNA fragment). The DNA fragments are such that they can readily be detected using any technique known to one of ordinary skill in the art of DNA detection. In one embodiment of the invention, DNA fragments are amplified to aid in detection using methods such as polymerase chain reaction ("PCR"). For example, the sample is amplified in an amplifying mixture containing one or more forward primers and one or more reverse primers. Primers should have similar melting temperatures to allow for PCR to occur simultaneously for each fragment. In one embodiment primers are from approximately 5-30 bases in length. The analysis can be carried out by detecting the length/size of the DNA fragment using techniques such as gel electrophoresis or determining the base sequence to confirm a predefined DNA sequence. In another embodiment, the DNA fragments can be detected by a hybridization method utilizing a labeled probe.

The DNA fragments comprise anywhere from 10-1000 nucleotides. In one embodiment the chimeric DNA marking agent contains two or more DNA fragments each of different lengths. In one embodiment, the DNA fragments comprise identical 5' and identical 3' ends and only differ in terms of the number of bases between the 5' and 3' ends. For example, the DNA fragments comprise the same 5-40 bases at the 5' end and the same 5-40 bases at the 3' end with a varying amount of bases between the 5' and 3' ends. The differences in the number of bases between the 5' and 3' ends should be enough to easily detect the difference in DNA fragment lengths in the chimeric DNA marking agent found on the target. In this embodiment the same forward and reverse primers can be used to amplify each sample. In one embodiment the primers are labeled as described below to aid in detection. In another embodiment the DNA fragments are detected by a hybridization method using a labeled probe.

In another embodiment wherein the DNA marking agent contains two or more DNA fragments each of different lengths, the 5' and/or 3' ends can differ in sequence. In this embodiment, specific forward primers are used to match each of the varying 5' ends and specific reverse primers are used to match each of the varying 3' ends. The DNA fragments may compose 1, 2, 3, 4, 5, 6, 7, 8, 9, 10, or more different 5' ends and/or 1, 2, 3, 4, 5, 6, 7, 8, 9, 10 or more different 3' ends with varying amount of bases between the 5' and 3' ends. The 5' ends may vary by 1, 2, 3, 4, 5, 7, 8, 9, 10 or more bases. The 3' ends may vary by 1, 2, 3, 4, 5, 7, 8, 9, 10 or more bases. In one embodiment, the 5' ends are all the same length and the 3' ends are all the same length. In another embodiment, the 5' ends are different lengths and the 3' ends are different lengths. The differences in the number of bases between the 5' and 3' ends should be enough to easily detect the difference in DNA fragment lengths in the chimeric DNA marking agent found on the target. Different combinations of forward and reverse primers can be used to aid in identification. For example, if the chimeric DNA marking agent comprises fragments with known 5' and or 3' ends, PCR amplification reactions can be set up that only amplify DNA fragments of a particular combination of matching forward and reverse primers. In some embodiments the probes are labeled as discussed below to aid in identification. In other embodiments the forward and reverse primers are labeled with different probes. Increasing the number of different lengths and/or number of different end portions of the fragments increases the number of possible combinations available for detection. In another embodiment, the DNA fragments can be detected by a hybridization method utilizing a labeled probe as discussed below.

In one embodiment the chimeric DNA marking agent contains DNA fragments that differ in one or more of the nucleotide bases forming the DNA fragment. In this embodiment the fragments size/length can be the same or different. In one embodiment the DNA fragments may differ in two or more bases, three or more bases, four or more bases, five or more bases, six or more bases, seven or more bases, eight or more bases, nine or more bases, 10 or more bases, 12 or more bases, 14 or more bases, 16 or more bases, 17 or more bases, 18 or more bases, 20 or more bases, or 25 or more bases. The differences in bases can be found at the 5' end, the 3' end, and/or throughout the DNA fragment. In this embodiment, the DNA fragments can be determined by either sequencing of the DNA fragments or by use of a hybridization technique as described below.

In one embodiment, the polynucleotide probes or primers of the invention are conjugated to detectable markers. Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., $^{3}H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads. In one embodiment, the polynucleotide probes are immobilized on a substrate such as: artificial membranes, organic supports, biopolymer supports and inorganic supports.

Alternatively, the DNA fragments can be detected by a hybridization method utilizing a labeled probe. For example, a labeled DNA strand having a complimentary sequence to that of the DNA fragment, wherein the hybridization is carried out under particular conditions and the presence or absence of the formation of a double stranded DNA can be detected. For example, detection can occur by the presence, absence, or discoloration of a detection solution (e.g., colloidal gold solution or a solution containing a fluorescent reagent). Examples of labels associated with the complimentary sequence used for detection include, but are not limited to, radioactive probes (e.g., radioactive isotopes of phosphorus), fluorescent, digoxigenin, or dyes.

In one embodiment of the invention, the chimeric DNA marking agent sample is retrieved by contacting the target with a moist article. An example of a moist article includes, but is not limited to, a swab, a tissue, or a plastic scraper. In another embodiment of the invention, the chimeric DNA marking agent sample is collected by contacting the target with a liquid which removes the DNA fragments from the target, wherein the DNA fragments are recovered by filtration and/or centrifugation. Such methods are well known in the art.

The chimeric DNA marking system can be used alone or in combination with a general marking agent and/or an immobilizing agent. Marking agents generally comprise liquid pigments and/or dyes, powder pigments and/or dyes, water soluble pigments and/or dyes, permanent pigments and/or dyes, infra red pigments and/or dyes, ultra violet pigments and/or dyes, pigments and/or dyes that glow in the dark (e.g., a chemiluminescent pigment and/or dye or a phosphorescent pigment and/or dye), and miniature radiotransmitters. Immobilizing agents are used to immobilize a target struck by the projectile. Examples of immobilizing components include liquid irritants, powder irritants, gaseous irritants, pepper powders, tear gas, malodorants, and other noxious chemicals. In one aspect of the invention, the chimeric DNA marking agent is provided with the general marking and/or immobilizing agent. In another aspect of the invention, the chimeric DNA marking agent is separated from the general marking agent or immobilizing agent, such as in a separate cavity of a projectile.

The chimeric DNA marking system can be combined with a protective agent. In one embodiment the chimeric DNA marking agent is in a solution that protects the DNA fragments from degradation or decomposition (e.g., protection from ultraviolet light, heat, acidity, alkalinity, etc. . . . ). In another embodiment the chimeric DNA marking agent is in a solution that protects the DNA fragments from alteration by or interaction with the general marking agent, the immobilization agent, and/or the inhibiting agent. In one embodiment the chimeric DNA marking agent, general making agent, immobilization agent, and/or inhibiting agent are contained in a resin, liposome, or some other barrier to prevent the interaction with the other agents. In another embodiment the chimeric DNA marking agent is in a solution that prevents removal of the chimeric DNA marking agent except under controlled conditions. In another embodiment the chimeric DNA marking agent is in a solution that prevents removal of the chimeric DNA marking agent with water. In another embodiment the chimeric DNA marking agent is in a solution that prevents removal of the chimeric DNA marking agent with water and soap. In another embodiment the chimeric DNA marking agent is in a solution that prevents removal of the chimeric DNA marking agent with an alcohol based solvent. In another embodiment the chimeric DNA marking agent is present in a solution in a form in which only a portion of the chimeric DNA marking agent can be removed with water and is also present in a form that can only be removed by an alcohol based solution thereby the marker will remain on the target if only one method was used to try to remove the marker. For example, but not limited to, the DNA fragments may be protected by a liposome to prevent the removal by water. In another embodiment, the chimeric DNA marking agent is suspended in both a water-based solution and an oil-based solution to protect against the washing away of the chimeric DNA marking agent. In another embodiment the chimeric DNA marking agent is in a solution that prevents removal of the chimeric DNA marking agent except by a specific solution that can be used to collect the DNA fragments for analysis.

Figure 1B:
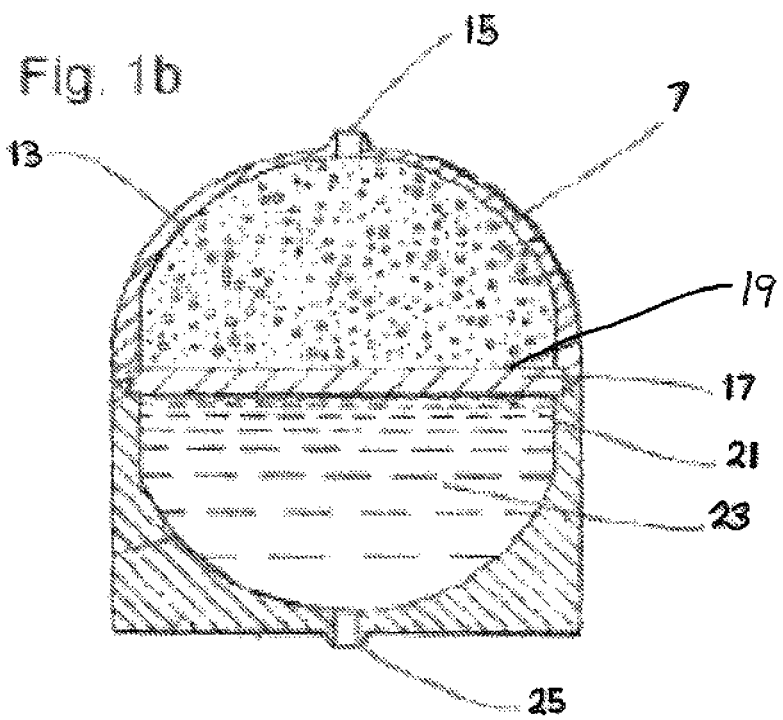

The chimeric DNA marking agents are provided in devices or housings that can transfer the chimeric DNA marking agent onto a target. For example, in one embodiment the chimeric DNA marking agent is provided in a housing in the form of a projectile, such as projectiles shown in FIGS. 1a, 1b, 2a, 2band 2c. Referring to FIGS. 1a & 1b, there is shown one embodiment of a projectile 1 having a chimeric DNA marking agent. In this embodiment, the projectile 1 comprises a generally hemispherical portion 3, having a first cavity 7, joined to a generally cylindrical portion 5 having a second cavity 23. U.S. Pat. Nos. 6,230,630 and 6,615,739 (the disclosure of both which are incorporated herein by reference in their entirety) disclose such projectiles having a first front enclosed cavity in a generally hemispherical portion, and a second rear closed cavity in a generally cylindrical portion. Further, U.S. Pat. Nos. 5,254,379 and 5,639,526 (the disclosures of which are incorporated herein by reference in their entirety) disclose a linear polymer of sufficient strength for a projectile to be transported, loaded, and fired out of a compressed gas gun, wherein the lineal polymer is molecularly oriented such that upon application of a force at any impact point on the projectile shell, the shell fractures in a way that greatly reduces the risk of injury.

Further, the material of the projectile must also be selected such that it protects the chimeric DNA marking agent from degrading or decomposition of the DNA fragments (e.g., protection from ultraviolet light, heat, acidity, alkalinity, etc. . . . ). One suitable plastic for use in manufacturing the component containing the chimeric DNA marking agent is a polystyrene marketed under the tradename Novacor and distributed by Polymerland, Inc. This polystyrene is a linear polymer which yields a hemispherical portion that is impervious to water and does not dissolve when contacted by rain or sweat or when placed in a warm humid environment. This impervious nature allows the shell to be used to contain a variety of products including water, smoke, tear gas and other items unsuitable for placement in known gelatin shells.

The hemispherical portion 3 generally includes a fill hole 15 for the introduction of material such as the chimeric DNA marking agent into the projectile after the hemispherical portion 3 is joined to the cylindrical portion 5. After introduction of the material through the fill hole 15, the fill hole is sealed and a generally smooth surface is presented by the projectile in the region of the fill hole 15.

The cylindrical portion 5 may be formed from a variety of materials resistant to water such as plastics such as polystyrene. To simplify manufacturing and to permit easy joining of the cylindrical portion 5 to the hemispherical portion 3, the two portions are in one embodiment manufactured from the same material. The cylindrical portion 5 includes a fill hole 25 for the introduction of material into the cylindrical portion after it is joined to the hemispherical portion 3. After introduction of the material through the fill hole 25, the fill hole is sealed and a generally smooth surface is presented by the projectile in the region of the fill hole 25. In another embodiment, the cylindrical portion 3, having a second interior compartment 23 which may be filled through a fill hole 25.

Prior to joining the hemispherical portion 3 to the cylindrical portion 5 at the rim 2, a divider 17 (e.g., circular insert) having a first wall 19 facing the interior volume of the hemispherical portion 3 and a second wall 21 facing the interior volume of the cylindrical portion 5 may be placed between the hemispherical and cylindrical portions. The circular insert 17 isolates the interior volume of the hemispherical portion 3 from the interior volume of the cylindrical portion 5, allowing differing materials to be inserted into each volume. The circular insert 17 may be formed from a variety of materials resistant to water and having the appropriate thermal properties. In one embodiment, the circular insert 17 is formed from a plastic or other moisture resistant material that will not bond with the material from which the hemispherical and cylindrical portions are formed. One suitable plastic for use in manufacturing the circular insert 17 is an acetal homopolymer. In one embodiment, the hemispherical portion 3, the cylindrical portion 5 and the circular insert 17 are each formed by injection molding a suitable plastic.

Once the component parts are prepared, they are joined together, in one embodiment by ultrasonic welding, although other suitable techniques such as solvent welding may be used employing conventional techniques. Following the joining of the three component pieces, material may be injected into the interior volumes of the hemispherical portion 3 and the cylindrical portion 5 through the appropriate fill holes. The fill holes may then be sealed using conventional techniques such as a fill and seal injection needle.

In one embodiment the circular insert 17 is present to create two cavities for containing different marking agents, immobilization agents, inhibiting agents, and/or combinations thereof. In another embodiment, the circular insert 17 is absent; therefore, there is only one cavity to contain marking agents, immobilization agents, or inhibiting agents, or combinations thereof. Alternatively or additionally, the portions of the projectile can be further subdivided, e.g., by inserting one or more dividers 17 into the portions.

In one embodiment the fill material is provided as a chimeric DNA marking agent. In another embodiment, such fill material is typically a fluid. In one embodiment the fluid contains a weighting agent in combination with a chimeric DNA marking agent. The weighting agent is typically required to obtain the desired weight relationship of the projectile 1 to maintain the center of gravity (Cg) of the projectile 1 in front of the center of pressure (Cp) of the projectile 1 during flight of the projectile 1. The center of gravity, which refers to the distribution of mass in the projectile, can be defined as the point at which the projectile would be perfectly balanced if it were suspended with no forces, other than gravity, acting on it. The center of pressure can be defined as the point at which the projectile would be balanced if it were suspended with no forces, other than air pressure, acting on it. In one embodiment, the fill material is provided such that the center of gravity is positioned as far forward as possible.

Figure 2A:
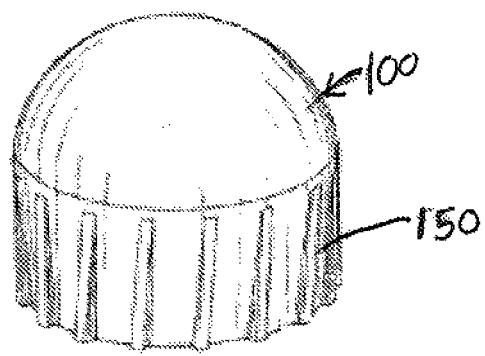
FIG. 2a is a front elevation view of another embodiment of an aerodynamic projectile having a chimeric DNA marking agent.
Figure 2B:
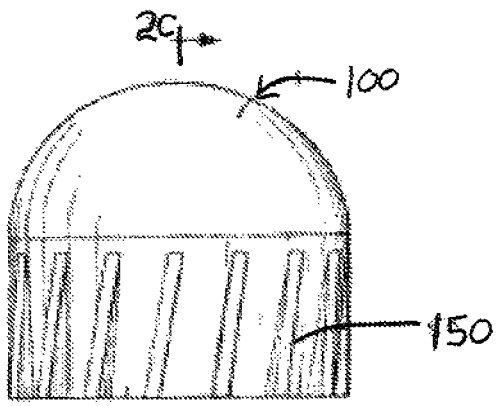
Figure 2C:
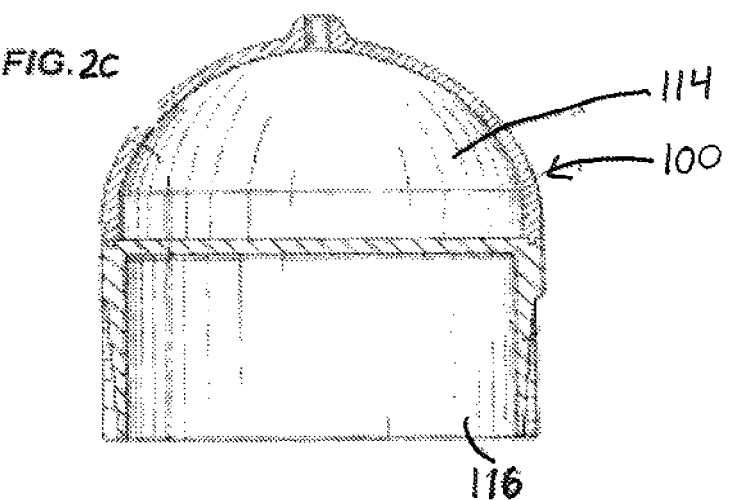

An alternate projectile 100 having a single closed cavity 114 is shown in FIGS. 2a-2c. Such a projectile 100 is both lightweight and effective in marking and/or immobilizing a target, buy yet also provides greater accuracy than traditional paint balls. U.S. patent application Ser. No. 12/317,868, the disclosure of which is incorporated herein by reference in its entirety, discloses such a single cavity projectile having an open rear cavity 116. The projectile of the '868 Application also includes a plurality of fins 150 on a sidewall member to enhance the accuracy of the projectile.

As with the projectile of the prior embodiment, the projectile of this embodiment contains the chimeric DNA marking agent in the cavity 114 of the projectile.

Figure 3:
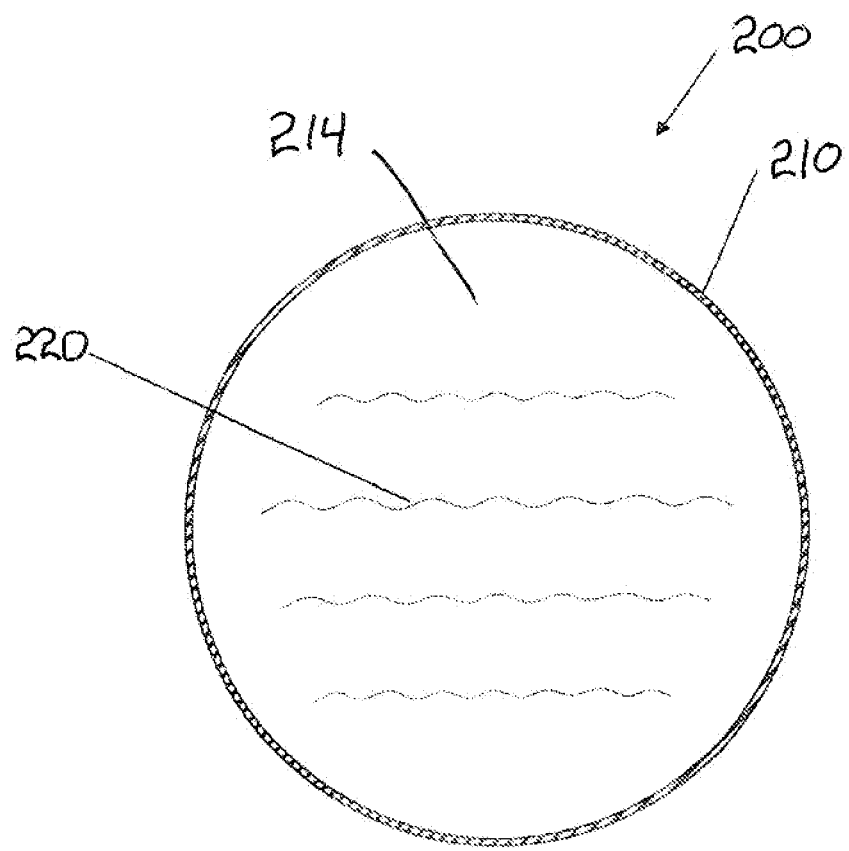
FIG. 3 is a cross-sectional view of another embodiment of a projectile having a chimeric DNA marking agent.

Another alternate projectile 200 having a single closed cavity 214 is shown in FIG. 3. The projectile 200 has a spherical body 210 that defines the cavity 214. The spherical body 210 is partially or fully filled with the chimeric DNA marking agent 220. While certain projectiles have been described herein as being capable of containing the chimeric DNA marking agent, it is understood that a variety of alternate projectiles may be utilized without departing from the scope of the present invention.

Alternatively, the chimeric DNA marking agent may be provided in a spray canister (not shown). The spray canister can contain just the chimeric DNA marking agent alone or the chimeric DNA marking agent in combination with an additional agent such as a general marking agent, an inhibiting agent, and/or an immobilizing agent. The chimeric DNA marking agent may be contained in the general marking agent, the inhibiting agent, the immobilizing agent, in a combination of the three, or in a separate solution. Examples of general marking agents comprise liquid pigments and/or dyes, powder pigments and/or dyes, water soluble pigments and/or dyes, permanent pigments and/or dyes, infra red pigments and/or dyes, ultra violet pigments and/or dyes, pigments and/or dyes that glow in the dark (e.g., a chemiluminescent pigment and/or dye or a phosphorescent pigment and/or dye), and miniature radiotransmitters. Examples of inhibiting agents include pepper powder or liquid, tear gas, malodorants, or anything that is used in an attempt to modify the behavior of animals, including humans. Examples of immobilizing components include liquid irritants, powder irritants, gaseous irritants, pepper powders, tear gas, malodorants, and other noxious chemicals. The marked target can then be identified by detection of the particular chimeric DNA marker sample found on the target as discussed above.

Such spray canisters may release the chimeric DNA marking agent in different forms, for example, sprays, mists, foams, fumes, froths, vapors, sprinkles, drizzles, drops, powder dustings, or fogs. The spray container may be pressurized to aid in the dispensing of the chimeric DNA marking agent. The spray canister can vary with size to be small enough for a keychain or sizable enough to control a large crowd.

Another device that can utilize the chimeric DNA marking agent includes a moist or dry article (not shown), for example wipes, cloths, swabs, dusters, gloves, or other objects that contain a liquid or dry delivery agent, containing the chimeric DNA marking agent. These devices can mark the target by coming in physical contact with the target. The marked target can then be identified by detection of the particular chimeric DNA marker sample found on the target as discussed above.

In one embodiment the combination of DNA fragments in the chimeric DNA marking system can be used to identify the individual or device that marked the target. For example, in one embodiment when a particular projectile, spray canister, and/or wipe is issued to an individual, the issuance is recorded in a database or log. Thus, when the chimeric DNA marking agent is sampled and identified as outlined above, the individual that marked the target can be identified by matching the combination of DNA fragments with the database or log. In another embodiment, the timeframe for which the projectile, spray canister, or wipes was issued to the individual will also be logged to aid in determination of the timeframe in which the target was marked.

One benefit of utilizing a chimeric DNA marker is that the identification of multiple DNA samples found in the chimeric DNA marker, as opposed to a DNA marker having only a single DNA fragment or sample, results in a more accurate identification.

Another benefit of utilizing a chimeric DNA marker over a single fragment DNA marker when producing multiple different DNA markers is that the cost reduction for producing different DNA markers is significant when DNA samples are combined in a chimeric DNA marker. The cost of producing a large volume of synthetic DNA does not change significantly from producing a small volume of the same synthetic DNA. However, producing multiple different synthetic DNA samples is extremely expensive. As a result, one can combine multiple discrete DNA samples in various combinations to produce multiple different chimeric DNA markers in a much more cost effective manner than producing multiple DNA markers each having a single discrete DNA fragment. For example, if 10 different synthetic DNA samples are produced one could make either (a) 10 DNA markers where each marker contained a single discrete DNA sample, or (b) 45 different chimeric DNA markers having a variety of combinations of the ten different synthetic DNA samples. Similarly, if 100 different synthetic DNA samples are produced one could make either (a) 100 DNA markers where each marker contained a single discrete DNA sample, or (b) 4950 different chimeric DNA markers having a variety of combinations of the 100 different synthetic DNA samples. Thus, when producing multiple different DNA markers, the use of multiple DNA samples in a single chimeric DNA marker results in DNA markers that are a fraction of the cost of DNA markers having a single discrete DNA sample.

Notwithstanding the benefits of combining multiple DNA samples, a single DNA fragment marking agent may alternatively be used. The DNA fragment of the single DNA fragment marking agent may be formed in a liquid solution, a gas or a powder, may be single stranded or double stranded, and may be produced using recombinant DNA technology (e.g., polymerase chain reaction (PCR) amplification, cloning, etc.) or chemical synthesis, similarly as discussed above regarding the chimeric DNA marker. Detection of the single DNA fragment may be done by any suitable detection technique, such as hybridization utilizing a labeled probe, gel electrophoresis or determining the base sequence to confirm a predefined DNA sequence, for example. The single DNA fragment may also be amplified to aid in detection (e.g., PCR).

The single DNA fragment marking agent may be used alone or in combination with any combination of other agents discussed above. The single DNA fragment marking agent may be used in any of the delivery systems and methods (e.g., projectile, spray canister or wipe) discussed above relative to the chimeric DNA marker. Multiple delivery devices may be provided with the same DNA marking agent so that any delivery device from the set of multiple delivery devices may be linked to a specific entity (e.g., person or organization) or device (e.g., gun). The unique DNA marking agent of a delivery device may be recorded with a date, time and/or location of its deployment, where a target that has been marked by the DNA marking agent may be linked to a particular scene or incident.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

What is claimed is:

1. A device for delivering a chimeric deoxyribonucleic acid (DNA) marking agent to an exterior surface of a target, comprising:
   a housing comprising a projectile, the projectile having a solid outer shell and being capable of being launched towards a target, the projectile further comprising a semi-hemispherical body portion having a first cavity, a generally cylindrical body portion having a second cavity, and a divider separating the first cavity from the second cavity;
   a chimeric DNA marking agent sealed within one of the first cavity and the second cavity, wherein the chimeric DNA marking agent comprises two or more unique DNA fragments;
   wherein at least one of the first cavity and the second cavity is at partially filled with one of a general marking agent, an inhibiting agent, an immobilizing agent, and a weighting agent; and
   the projectile capable of fracturing upon contact with the exterior surface of the target to release the chimeric DNA marking agent onto the exterior surface of the target.

2. The delivery device of claim 1, wherein the chimeric DNA marking agent further comprises a fill material including one or more of a liquid, a gas and a powder.

3. The delivery device of claim 1, further comprising a general marking agent sealed within the projectile.

4. The delivery device of claim 1, further comprising an inhibiting agent sealed within the projectile.

5. The delivery device of claim 1, further comprising an immobilizing agent sealed within the projectile.

6. The delivery device of claim 1, further comprising a weighting agent sealed within the projectile.

7. The delivery device of claim 1, further comprising a protective agent sealed within the projectile.

8. A marking agent delivery device for marking an exterior surface of a target comprising:
   a housing comprising a thin-walled polystyrene body defining at least one cavity and at least one fill hole, wherein at least a portion of the body is semi-hemispherical and another portion of the body is generally cylindrical, the housing capable of being launched towards the target;
   a fill material comprising one of a liquid, a gas and a powder sealed within the cavity;
   a DNA marking agent sealed within the cavity, wherein the DNA marking agent includes one or more unique DNA fragments;
   at least one of a general marking agent, an inhibiting agent, an immobilizing agent, a weighting agent and a protective agent sealed within the cavity; and
   wherein the housing is capable of fracturing upon contact with the exterior surface of the target to release the chimeric DNA marking agent onto the exterior surface of the target.

9. The device of claim 1, further comprising a launching device capable of launching the projectile.

10. The device of claim 9, wherein the launching device is a compressed gas gun.

11. The device of claim 8, further comprising a launching device capable of launching the housing.

12. The device of claim 11, wherein the launching device is a compressed gas gun.

13. A device for delivering a chimeric deoxyribonucleic acid (DNA) marking agent to an exterior surface of a target, comprising:
   a projectile being capable of being launched towards a target, the projectile comprising a thin-walled polystyrene outer shell having a hemispherical body portion having a first cavity, a generally cylindrical body portion having a second cavity, and a divider separating the first cavity from the second cavity;
   a chimeric DNA marking agent sealed within one of the first cavity and the second cavity of the projectile, wherein the chimeric DNA marking agent comprises two or more unique DNA fragments; and
   the thin-walled outer shell of the projectile capable of fracturing upon contact with the exterior surface of the target to release the chimeric DNA marking agent onto the exterior surface of the target.

14. The delivery device of claim 1, wherein the projectile is comprised of polystyrene.

15. The device of claim 8, wherein the housing is comprised of polystyrene.

* * * * *